US00PP09380P

United States Patent [19]

Iverson

[11] Patent Number: Plant 9,380

[45] Date of Patent: Nov. 21, 1995

[54] DAYLILY PLANT NAMED 'PINK SILK RUFFLES'

[76] Inventor: Ronald C. Iverson, Rte. 1, Box 326B, Orange, Va. 22960

[21] Appl. No.: 355,319

[22] Filed: Dec. 12, 1994

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new cultivar of daylily plant named Pink Silk Ruffles, characterized by its large deep pink flowers with yellow throat, ruffled petal edges which are crimped, downwardly curved petal ends, very fragrant flowers, reblooming ability, and its very floriferous habit with up to 22 buds being formed on each scrape.

2 Drawing Sheets

The present invention comprises a new and distinct cultivar of daylily which belongs to the genus Hemerocallis, and is hereinafter referred to by the cultivar name Pink Silk Ruffles.

The new cultivar is the result of an open pollination breeding program in which numerous unnamed and unidentified daylily cultivars were planted in an open cultivated field in a controlled environment in Merriville, Ind. Seed was collected from the open pollinated female plants and grown in a controlled area in Merriville, Ind.

Well over one thousand seedling plants were mass-selected in early summer 1990, and grown out in Long Grove, Ill. in a cultivated area. The new cultivar was discovered and selected from the mass-selected plants by inventor Ronald C. Iverson in August 1980 in such area in Long Grove, Ill.

The first act of asexual reproduction of Pink Silk Ruffles was accomplished when divisions were taken from the selection in September 1990 in a controlled environment in Long Grove, Ill. by Ronald C. Iverson. Horticulture examination of selected units initiated in June 1991 has demonstrated that the combination of characteristics as herein disclosed for Pink Silk Ruffles are firmly fixed and are retained through successive generations of asexual reproduction.

Pink Silk Ruffles has not been observed under all possible environmental conditions. The phenotype may vary significantly with variations in environment such as temperature, light intensity, and daylength without, however, any variance in genotype. The following observations, measurements, and comparisons describe plants grown in Long Grove, Ill. under greenhouse conditions which approximate those generally used in commercial practice.

The following traits have been repeatedly observed and are determined to be basic characteristics of Pink Silk Ruffles which in combination distinguish this daylily as a new and distinct cultivar.

1. Deep pink flower color with a yellow throat, with the edges of the petals being crimped.
2. Flowers are very fragrant.
3. Flowers have a crepe texture with a shiny smooth underside.
4. Individual flowers are very large, being approximately 4¼ inches in diameter. There are up to 22 buds on a flower scape, making the cultivar very floriferous.
5. The mature height of the flower scapes is approximately 22 inches.
6. Individual fans produce 2–3 flowering scapes in each season. This ability to rebloom is a significant feature of the new cultivar.

7. Bloom season in Illinois is from early July until October.

The new cultivar is substantially dissimilar to but can be compared to other fragrant daylily cultivars, for example, the daylily Fragrant Treasure, disclosed in U.S. Plant Pat. No. 8,140. Fragrant Treasure has Fragrant flowers, reblooming habit, and light yellow flowers. The flowers of Pink Silk Ruffles are substantially larger, and are deep pink in color.

The accompanying color photographic drawings show typical flower characteristics of Pink Silk Ruffles, with colors being as true as possible with illustrations of this type.

The Photo on sheet 1 is a top perspective of a typical plant of the new cultivar grown in a 10 inch pot.

The photo on sheet 2 is a greatly enlarged top view showing in much greater detail the flower parts.

It is noted that the illustrated flower color is lighter than the true deeper pinker flower color, the accurate color values for which are described below.

In the following description, color references are made to The Royal Horticultural Society Colour Chart. The color values were determined between 10:00–10:30 a.m. on June 14 under hazy light conditions at Long Grove, Ill.

Parentage:

*Origin.*—Selection from mass-selected seedling population obtained by open pollination.

*Seed parent.*—Unknown.

*Pollen parent.*—Unknown.

Classification:

*Botanic.*—Hemerocallis hybrid.

*Commercial.*—Large flower daylily cv. Pink Silk Ruffles.

Plant description:

*Form.*—Wide, spreading.

*Height.*—Approximately 18 inches.

*Growth habit.*—Clump forming, vigorous.

*Strength.*—Good.

*Foliage.*—Quantity: Average. Size of leaf: 1¼ inches wide ×20 inches long. Shape of leaf: Typical Hemerocallis. Texture: Smooth. Color: Green 144A.

*Bulbs.*—Size: 6 inches long. Color: Tan.

Bud description:

*Form.*—Cylindrical.

*Size.*—3 inches long.

*Opening.*—Early morning.

*Color.*—Yellow streaked with green.

Flowering description:

*Blooming habit.*—Early July until October.

*Size.*—Very large, 4½ inches in diameter.

*Borne.*—15° angle from the scape.

*Shape.*—Star.

*Tepalage.*—Number of tepals: 6. Arrangement: Star.

Color: Upper Surface: Main color 186A blending through 151C to throat 8A. Lower Surface: 21C. Tepal longevity: One day. Spotting: No markings. Color change: Color is very persistent with no or very little fading even on hot days. Texture: Wrinkled, very ruffled crimped edges. Appearance: Petals curve back resulting in relatively low flower; veins are darker than main petal color. Disease resistance: No recognized problem. Fragrance: Musty, slightly sweet fragrance. Lasting quality: One day.

Reproductive organs:

*Stamens, anthers.*—Arrangement: Central, erect. Length: 2 inches. Number: Six. Filaments: Color 17A.

*Pistils.*—Yellow at base, purple at ends.

*Stigma.*—Yellow inside, purple at ends.

Fruit:

*Fertility.*—Moderately fertile.

*Shape.*—Round.

*Color at maturity.*—Black.

I claim:

1. A new and distinct cultivar of daylily plant named Pink Silk Ruffles, as illustrated and described.

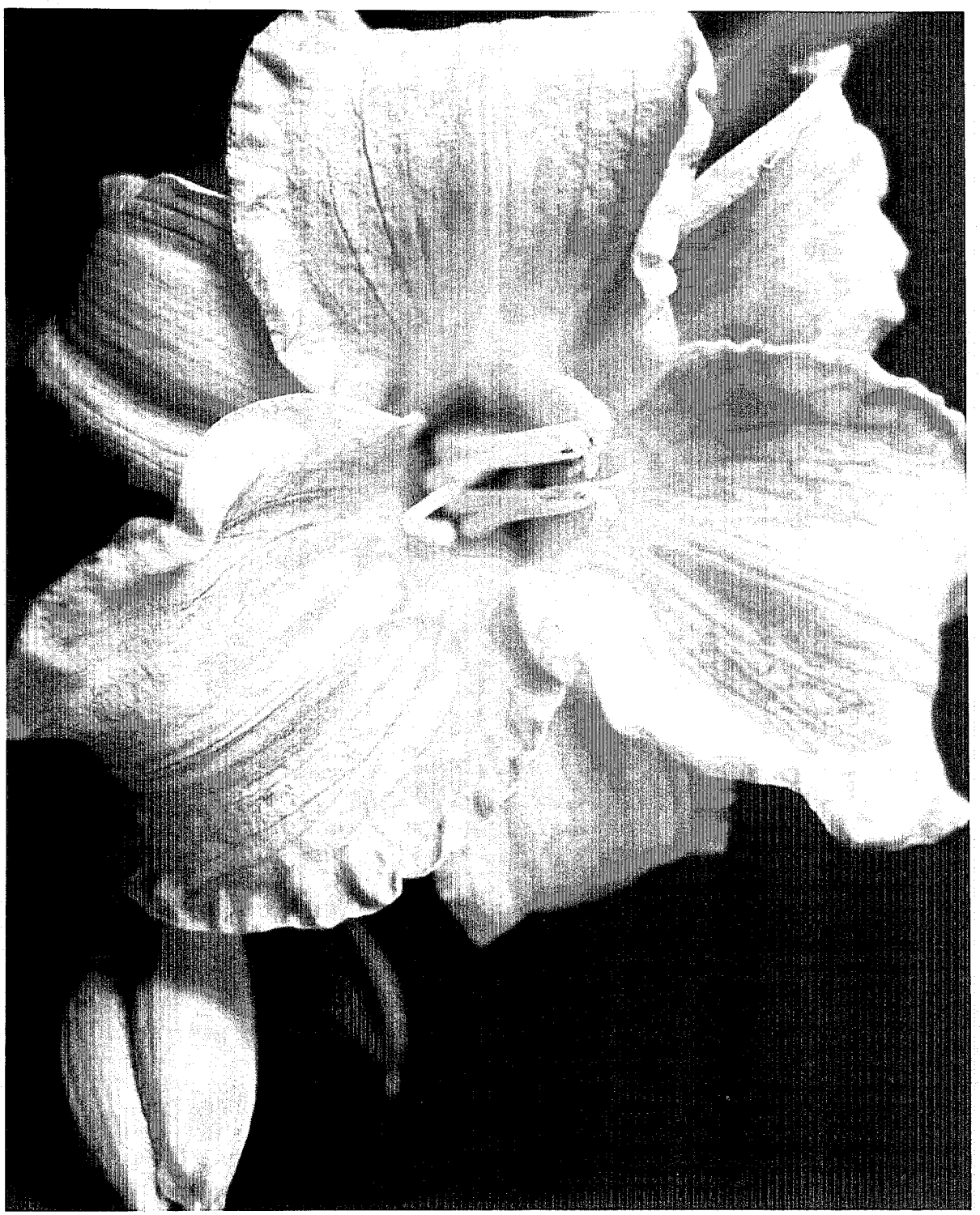

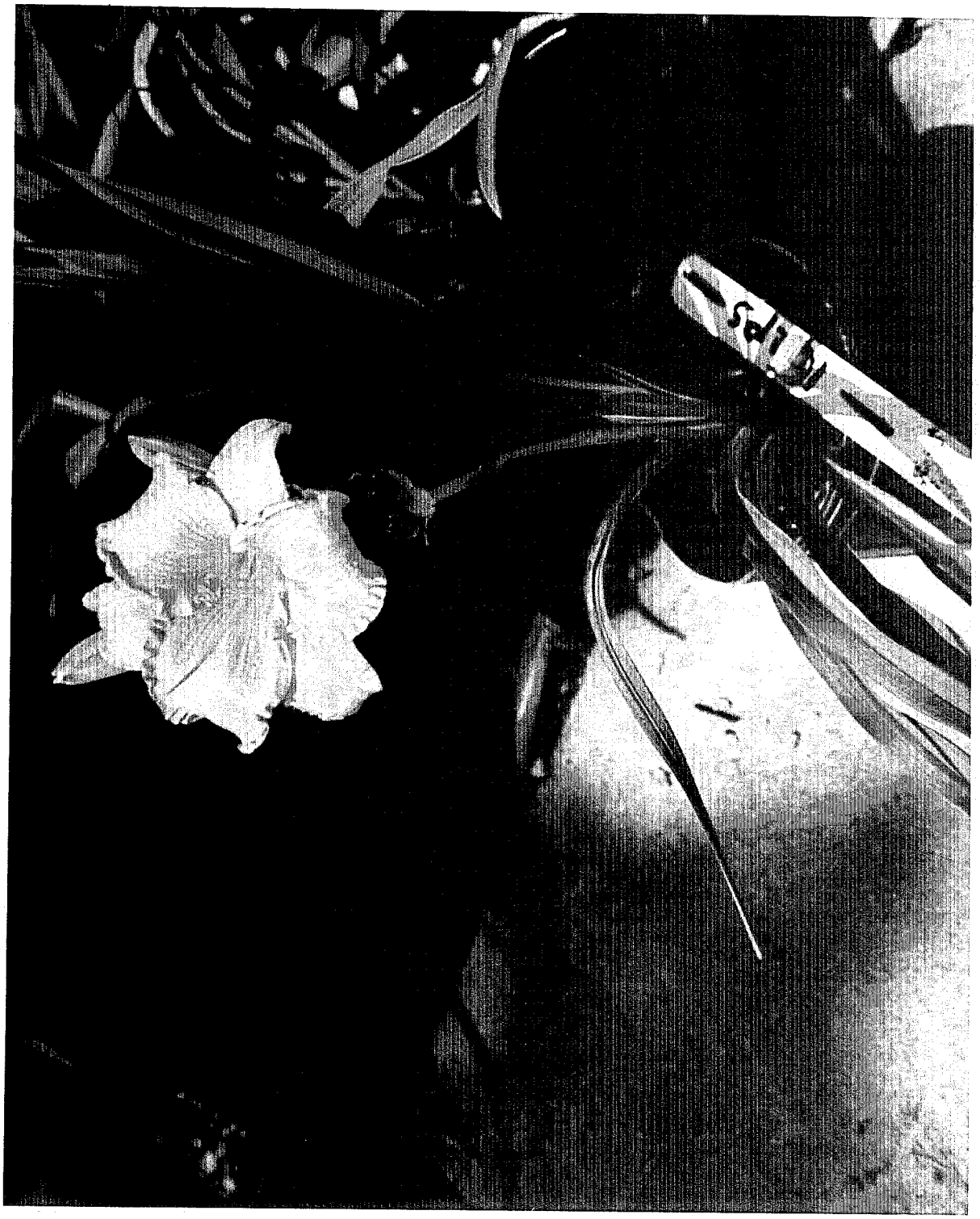

* * * * *